United States Patent
Donovan et al.

(10) Patent No.: US 10,444,235 B2
(45) Date of Patent: Oct. 15, 2019

(54) SYSTEMS AND METHODS FOR TREATING, DIAGNOSING AND PREDICTING THE RESPONSE TO THERAPY OF BREAST CANCER

(75) Inventors: Michael Donovan, Boston, MA (US); Doug Powell, Bronxville, NY (US); Faisal Khan, Fishkill, NY (US)

(73) Assignee: FUNDACAO D. ANNA SOMMER CHAMPALIMAUD E DR. CARLOS MONTEZ CHAMPALIMAUD, Lisbon (PT)

( * ) Notice: Subject to any disclaimer, the term of this patent is extended or adjusted under 35 U.S.C. 154(b) by 1083 days.

(21) Appl. No.: 12/821,664

(22) Filed: Jun. 23, 2010

(65) Prior Publication Data

US 2011/0040544 A1    Feb. 17, 2011

Related U.S. Application Data

(60) Provisional application No. 61/269,395, filed on Jun. 23, 2009.

(51) Int. Cl.
*G01N 33/574*    (2006.01)

(52) U.S. Cl.
CPC ... *G01N 33/57415* (2013.01); *G01N 2800/52* (2013.01)

(58) Field of Classification Search
None
See application file for complete search history.

(56) References Cited

U.S. PATENT DOCUMENTS 8,163,499 B2 * 4/2012 Singh et al. ............... 435/7.1

FOREIGN PATENT DOCUMENTS

WO    WO-2006/091693 A2    8/2006

OTHER PUBLICATIONS

Scaltriti et al (Journal National Cancer Institute, Apr. 2007, 99:628-638).*
Hudelist et al (Int J Cancer, 2006, 118:1126-1134).*
Gancberg et al (Anatomic Pathology, 2000, 113:675-682).*
USPTO memo for decision in *Alice Corporation Pty. Ltd.* v. *CLS Bank International, et al*, Jun. 25, 2014.*
European Search Report dated Jan. 10, 2013 for the corresponding European Application No. 10797600.3.
Frogne et al., Determination of HER2 phosphorylation at tyrosine 1221/1222 improves prediction of poor survival for breast cancer patients with hormone receptor-positive tumors, *Breast Cancer Research*, Feb. 24, 2009, pp. R11, vol. 11 , No. 1, Current Science, London, GB.
Peiro et al., Analysis of HER-2/neu amplification in endometrial carcinoma by chromogenic in situ hybridization. Correlation with fluorescence in situ hybridization, HER-2/neu, p53 and Ki-67 protein expression, and outcome, *Modern Pathology*, Jan. 30, 2004, pp. 227-287, vol. 17, No. 3.
Fink-Retter et al., Differential spatial expression and activation pattern of EGFR and HER2 in human breast cancer, *Oncology Reports*, Aug. 2007, pp. 299-304, vol. 18, No. 2.
Taniyama et al., Tyrosine 1248-phosphorylated HER2 expression and HER2 gene amplification in female invasive ductal carcinomas, *Breast Cancer*, Jul. 1, 2008, pp. 231-240, vol. 15, No. 3.
Frogne et al., Activation of ErbB3, EGFR and Erk is essential for growth of human breast cancer cell lines with acquired resistance to fulvestrant, *Breast Cancer Research and Treatment*, Apr. 14, 2008, pp. 263-275, vol. 114, No. 2, Kluwer Academic Publishers.
Singer et al., HER2 overexpression and activation, and tamoxifen efficacy in receptor-positive early breast cancer, *Journal of Cancer Research and Clinical Oncology*, Nov. 26, 2008, pp. 807-813, vol. 135, No. 6, Springer, Berlin, DE.

* cited by examiner

*Primary Examiner* — Laura B Goddard
(74) *Attorney, Agent, or Firm* — Leason Ellis LLP (57) ABSTRACT

This present invention systems and methods of accessing/monitoring the responsiveness of a breast cancer to a therapeutic compound.

18 Claims, 3 Drawing Sheets

SYSTEMS AND METHODS FOR TREATING, DIAGNOSING AND PREDICTING THE RESPONSE TO THERAPY OF BREAST CANCER

RELATED APPLICATIONS

This application claims priority to U.S. Ser. No. 61/269,395 filed Jun. 23, 2009 the contents of which is incorporated herein by reference in its entirety.

FIELD OF THE INVENTION

The present invention relates generally to method and systems for the diagnosis, prognosis and monitoring of breast cancer.

BACKGROUND OF THE INVENTION

HER2 is a member of the epidermal growth factor receptor family and is amplified/over-expressed in approximately 15-20% of breast cancers. HER-2 is a non-ligand member of the ERbB family and becomes activated mainly by overexpression which leads to spontaneous homo-dimerization, phosphorylation of the c-terminal part of Her2 and activation of downstream signaling events in a ligand-independent manner. In addition, Her2 also undergoes proteolytic cleavage which results in the release of the extracellular domain and the production of a truncated membrane fragment, p95, which is constitutively active. It has been hypothesized that the phosphorylated form of HER2 (pHER2) more accurately reflects the signaling and functional activity of the HER2 protein and recent evidence has demonstrated an association between pHER2 and HER2 gene copy number as assessed by fluorescent in situ hybridization (FISH).

The over-expression of HER2 is an independent adverse prognostic factor and currently the best predictive factor for the activity of trastuzumab, an anti-HER2 monoclonal antibody therapy. Currently, HER2 status is most frequently determined by immunohistochemical detection of HER2 protein expression on the cell membrane surface or by FISH of the HER2 gene copy number in fixed tissue using locus-specific probes for the HER2 gene and chromosome 17. These methods continue to be problematic due to issues with intra and inter laboratory reproducibility and pre-analytic variable such as fixation time. FISH is considered to be the reference standard and more accurately predicts response to therapy, but is technically demanding, expensive, and requires specialized equipment.

Trastuzumab used alone or in combination with chemotherapy, has shown significant clinical benefit in improving survival in metastatic patients, as well as halving the recurrence rate and improving survival in early breast cancer. Although over-expression is a useful predictor for response, only about one-third of patients, however, initially respond to trastuzumab monotherapy and the majority of initial responders demonstrate disease progression within 1 year of treatment initiation. Saez et al., 2006 and others have proposed that a terminally truncated form of the receptor, p95HER2, which remains membrane bound and tyrosine-phosphorylated, provides a mechanism for resistance to the monoclonal antibody trastuzumab.

Recently, Frogne et al., 2009 demonstrated that in a multivariate setting, levels of the phosphorylated form of Her2 (pHer2) in hormone receptor positive, primary tumors was an independent predictor for poor disease-free and overall survival when tested against tumor size, grade, nodal status and Her2. The results suggest that in trastuzumab-resistant disease, new strategies and compounds, including alternative therapeutic options should be considered such as small molecule dual kinase inhibitors (e.g., lapatinib), and selective targets within the angiogenic pathway (e.g., bevacizumab).

Prior studies demonstrated that the expression of truncated p95HER2 protein correlated with extent of lymph node involvement and metastatic disease, suggesting it represents a marker for more aggressive disease. Since trastuzumab blocks HER2 activity by binding to a part of the receptor that is located on the outside of the cell; the hypothesis is that the truncated p95HER2 (and/or the pHer2 full length receptor) remains active and may respond to inhibitors of tyrosine kinase activity, such as lapatinib. Scaltriti et al. 2007 showed that treatment of p95HER2 expressing cells with lapatinib inhibited p95HER2 phosphorylation, reduced downstream pAKT and inhibited cell growth.

SUMMARY OF THE INVENTION

In the U.S.—211,000 women diagnosed with Breast cancer each year of which 42,000 over-express HER2. Only less than 35% of these HER2 over-expressors respond to trastuzumab (Herceptin) therapy and of the initial responders, 25% of metastatic breast cancer patients develop resistance to trastuzumab. Thus, a need exists to better predict the response to therapy Accordingly in one aspect the invention provides methods of accessing the aggressiveness of a breast cancer in a subject by detecting the level of protein expression of AE1/AE3 (cytokeratin), TAB250 (Her2-ECD), c-erb B2 (Her2) and phosphorylated Her 2 (pHer2) in a formalin fixed, paraffin-embedded tumor tissue sample from the subject, and comparing the level of protein expression to a reference value. In various aspects the method is capable of discriminating between a Her2(2+) tumor and a Her2(3+) tumor.

In another aspect the invention provides a method of accessing the effectiveness of a treatment regimen treatment of a subject having breast cancer by detecting the level of protein expression of AE1/AE3 (cytokeratin), TAB250 (Her2-ECD), c-erb B2 (Her2) and phosphorylated Her 2 (pHer2 in a formalin fixed, paraffin-embedded tumor tissue sample from the subject, and comparing the level of protein expression to a reference value.

Also provided by the invention is a method of monitoring a treatment regimen of a subject with breast cancer by detecting the level of protein expression of AE1/AE3 (cytokeratin), TAB250 (Her2-ECD), c-erb B2 (Her2) and phosphorylated Her 2 (pHer2) in a tumor sample from the subject at a first period of time; detecting the level of protein expression of AE1/AE3 (cytokeratin), TAB250 (Her2-ECD), c-erb B2 (Her2) and phosphorylated Her 2 (pHer2) in a formalin fixed, paraffin-embedded tumor tissue sample from the subject at a second period of time and comparing the amount of protein expression detected at the first period of time to the amount detected in step at a second period of time or to a reference value.

The invention further provides a method of determining whether a subject with breast cancer would derive a benefit from a treatment regimen by detecting the level of protein expression of AE1/AE3 (cytokeratin), TAB250 (Her2-ECD), c-erb B2 (Her2) and phosphorylated Her 2 (pHer2) in a formalin fixed, paraffin-embedded tumor tissue sample from the subject, and comparing the level of protein expression to a reference value.

In another aspect the invention provides a method for predicting the survivability of a breast cancer-diagnosed subject by detecting the level of protein expression of AE1/AE3 (cytokeratin), TAB250 (Her2-ECD), c-erb B2 (Her2) and phosphorylated Her 2 (pHer2) in a formalin fixed, paraffin-embedded tumor tissue sample from the subject, and comparing the level of protein expression to a reference value.

In another aspect the invention provides methods for determining the amount of p95HER2 in a formalin fixed, paraffin-embedded tumor tissue sample from the subject by detecting the level of protein expression of TAB250 (Her2-ECD), c-erb B2 (Her2) and phosphorylated Her 2 (pHer2) in the sample; combining the expression levels of Her2 and pHer2 to produce a combined value; and subtracting the expression level of TAB250 from the combined value. By determining the amount of pHER2 in the sample, herceptin sensitivity or resistance can be determined allowing for the appropriate therapy to be selected.

The treatment is for example, biologic therapy such as lapatainib, trastuzumab or bevacizumab. The level of protein expression is detected by immunoflourescence.

Also included in the invention is a method of evaluating the survivability of a breast-cancer diagnosed subject by evaluating a dataset for a subject with a model predictive of breast cancer survivability, wherein the model is based on one or more features selected from the following group of features: tumor size, multifocalilty, surgical margin involvement, vessel/perineural invasion, necrosis, histological type, Bloom-Richardson grade, lymph node status, intraductal status, fibrocystic status, micro-calcifications, c-erb B2 (Her2) (HER2) staining index of tumor, phosphorylated Her 2 (pHer2) staining index of tumor, a morphometric measurement of epithelial nuclei derived from a tissue image, and/or a morphometric measurement of stroma derived from a tissue image, thereby evaluating the survivability of a breast-cancer diagnosed subject. Optionally, the method further includes outputting a value indicative of the subjects's survivability The invention also provides a computer-readable medium comprising computer executable instructions recorded thereon for performing the method comprising: evaluating a dataset for a patient with a model predictive of breast cancer survivability to thereby evaluate the survivability of the patient, wherein the model is based on one or more features selected from the following group of features: wherein the model is based on one or more features selected from the following group of features: tumor size, multifocalilty, surgical margin involvement, vessel/perineural invasion, necrosis, histological type, Bloom-Ricahrdosn grade, lymph node status, intraductal status, fibrocystic status, micro-calcifications, c-erb B2 (Her2) (HER2) staining index of tumor, phosphorylated Her 2 (pHer2) staining index of tumor, a morphometric measurement of epithelial nuclei derived from a tissue image, and/or a morphometric measurement of stroma derived from a tissue image.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

DETAILED DESCRIPTION OF THE INVENTION

The present invention relates to the identification of biomarkers associated with breast cancer. Specifically, the invention provides a multiplex immunofluorescent quantitative assay for Her-2 in formalin fixed paraffin embedded breast tumor samples. The assay is useful for tumor phenotyping, patient stratification and therapeutic indication. The invention further provides systems and apparatuses that use clinical information, molecular information and computer-generated morphometric information in a predictive model for predicting the occurrence, response to treatment, or survivability of a subject with breast cancer.

The systems methodology represents an integrative platform which relies on principles of machine learning to combine clinical data, with quantitative biomarker characteristics. By applying a systems analytical approach, a unique, tumor and patient specific profile is generated through on-slide technologies in image analysis, histomorphometry and multiplex spectral immunofluorescence (IF), using formalin-fixed, paraffin-embedded tissue sections (FFPE). Mathematical models are incorporated to threshold and then normalize individual and multiple (bio) markers in a given tissue section which allows for an accurate assessment of any given marker across multiple patient samples. A distinct advantage is that the histologic microanatomy is intact and protein signatures are directly associated with a specific cell type.

Accordingly, the invention provides methods of determining the responsiveness, e.g., sensitivity or resistance of a cancer cell to a therapeutic agent e.g., chemotherapy, ionizing radiation, or immunotherapy by determining the level of expression of AE1/AE3 (cytokeratin), TAB250 (Her2-ECD), c-erb B2 (Her2) and phosphorylated Her 2 (pHer2) in a patient derived sample. These methods are also useful for monitoring subjects undergoing treatments and therapies for breast cancer, and for selecting therapies and treatments that would be efficacious in subjects having breast cancer, wherein selection and use of such treatments and therapies slow the progression of breast cancer. More specifically, the invention provides methods of determining the whether a patient with a breast cancer will be responsive to trastuzumab.

Definitions

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), or as a likelihood, odds ratio, among other measures.

"Biomarker" in the context of the present invention encompasses, without limitation, proteins, nucleic acids, and metabolites, together with their polymorphisms, mutations, variants, modifications, subunits, fragments, protein-ligand complexes, and degradation products, protein-ligand complexes, elements, related metabolites, and other analytes or sample-derived measures. Biomarkers can also include mutated proteins or mutated nucleic acids.

A "Clinical indicator" is any physiological datum used alone or in conjunction with other data in evaluating the physiological condition of a collection of cells or of an organism. This term includes pre-clinical indicators. For example, in the context of breast cancer, the clinical indicator may include data indicating tumor size, multifocalilty, margin status, vessel/perineural invasion, necrosis, histologic type, Bloom-Richardson grade, pTNM and associated pathology including intraductal component, fibrocystic change, and micro-calcifications.

"Clinical parameters" encompasses all non-sample or non-analyte biomarkers of subject health status or other characteristics, such as, without limitation, age (Age), ethnicity (RACE), gender (Sex), or family history (FamHX).

"FN" is false negative, which for a disease state test means classifying a disease subject incorrectly as non-disease or normal.

"FP" is false positive, which for a disease state test means classifying a normal subject incorrectly as having disease.

A "formula," "algorithm," or "model" is any mathematical equation, algorithmic, analytical or programmed process, or statistical technique that takes one or more continuous or categorical inputs (herein called "parameters") and calculates an output value, sometimes referred to as an "index" or "index value." Non-limiting examples of "formulas" include sums, ratios, and regression operators, such as coefficients or exponents, biomarker value transformations and normalizations (including, without limitation, those normalization schemes based on clinical parameters, such as gender, age, or ethnicity), rules and guidelines, statistical classification models, and neural networks trained on historical populations. Of particular use in combining biomarkers are linear and non-linear equations and statistical classification analyses to determine the relationship between levels of biomarkers detected in a subject sample and the subject's responsiveness to chemotherapy. In panel and combination construction, of particular interest are structural and synactic statistical classification algorithms, and methods of risk index construction, utilizing pattern recognition features, including established techniques such as cross-correlation, Principal Components Analysis (PCA), factor rotation, Logistic Regression (Log Reg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, Support Vector Machines, and Hidden Markov Models, among others. Other techniques may be used in survival and time to event hazard analysis, including Cox, Weibull, Kaplan-Meier and Greenwood models well known to those of skill in the art. Many of these techniques are useful either combined with a biomarker selection technique, such as forward selection, backwards selection, or stepwise selection, complete enumeration of all potential panels of a given size, genetic algorithms, or they may themselves include biomarker selection methodologies in their own technique. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Bootstrap, Leave-One-Out (LOO) and 10-Fold cross-validation (10-Fold CV). At various steps, false discovery rates may be estimated by value permutation according to techniques known in the art. A "health economic utility function" is a formula that is derived from a combination of the expected probability of a range of clinical outcomes in an idealized applicable patient population, both before and after the introduction of a diagnostic or therapeutic intervention into the standard of care. It encompasses estimates of the accuracy, effectiveness and performance characteristics of such intervention, and a cost and/or value measurement (a utility) associated with each outcome, which may be derived from actual health system costs of care (services, supplies, devices and drugs, etc.) and/or as an estimated acceptable value per quality adjusted life year (QALY) resulting in each outcome. The sum, across all predicted outcomes, of the product of the predicted population size for an outcome multiplied by the respective outcomes expected utility is the total health economic utility of a given standard of care. The difference between (i) the total health economic utility calculated for the standard of care with the intervention versus (ii) the total health economic utility for the standard of care without the intervention results in an overall measure of the health economic cost or value of the intervention. This may itself be divided amongst the entire patient group being analyzed (or solely amongst the intervention group) to arrive at a cost per unit intervention, and to guide such decisions as market positioning, pricing, and assumptions of health system acceptance. Such health economic utility functions are commonly used to compare the cost-effectiveness of the intervention, but may also be transformed to estimate the acceptable value per QALY the health care system is willing to pay, or the acceptable cost-effective clinical performance characteristics required of a new intervention.

For diagnostic (or prognostic) interventions of the invention, as each outcome (which in a disease classifying diagnostic test may be a TP, FP, TN, or FN) bears a different cost, a health economic utility function may preferentially favor sensitivity over specificity, or PPV over NPV based on the clinical situation and individual outcome costs and value, and thus provides another measure of health economic performance and value which may be different from more direct clinical or analytical performance measures. These different measurements and relative trade-offs generally will converge only in the case of a perfect test, with zero error rate (a.k.a., zero predicted subject outcome misclassifications or FP and FN), which all performance measures will favor over imperfection, but to differing degrees.

"Her2 status", in routine practice, include immunohistochemistry and fluorescent in situ hybridization (FISH) Immunohistochemistry is used as a screening method to determine the level of Her2 protein expression in breast cancers and Her2 immunohistochemical results are generally expressed in a four scale scoring system ranging from 0 to 3+. Scoring criteria in this system comprise percentage of positive tumor cells and quality of staining including intensity of staining and type of membrane staining. According to clinical trials, expert consensus and US Food and Drug Administration (FDA) and the recent American Society of Clinical Oncology/College of American Pathologists (ASCO/CAPS) recommendations, 4 an invasive breast cancer with an Her2 3+ score is considered a positive Her2 tumor, ie, the patient is eligible for Trastuzumab therapy. Moreover, samples scored as Her2 2+ are considered Her2 equivocal and should be further tested with a validated assay for HER2 gene amplification.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's non-analyte clinical parameters.

"Negative predictive value" or "NPV" is calculated by TN/(TN+FN) or the true negative fraction of all negative test results. It also is inherently impacted by the prevalence of the disease and pre-test probability of the population intended to be tested. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test. Often, for binary disease state classification approaches using a continuous diagnostic test measurement, the sensitivity and specificity is summarized by Receiver Operating Characteristics (ROC) curves according to Pepe et al, "Limitations of the Odds Ratio in Gauging the Performance of a Diagnostic, Prognostic, or Screening Marker," Am. J. Epidemiol 2004, 159 (9): 882-890, and summarized by the Area Under the Curve (AUC) or c-statistic, an indicator that allows representation of the sensitivity and specificity of a test, assay, or method over the entire range of test (or assay) cut points with just a single value. See also, e.g., Shultz, "Clinical Interpretation Of Laboratory Procedures," chapter 14 in Teitz, Fundamentals of Clinical Chemistry, Burtis and Ashwood (eds.), 4$^{th}$ edition 1996, W.B. Saunders Company, pages 192-199; and Zweig et al., "ROC Curve Analysis: An Example Showing The Relationships Among Serum Lipid And Apolipoprotein Concentrations In Identifying Subjects With Coronary Artery Disease," Clin. Chem., 1992, 38(8): 1425-1428. An alternative approach using likelihood functions, odds ratios, information theory, predictive values, calibration (including goodness-of-fit), and reclassification measurements is summarized according to Cook, "Use and Misuse of the Receiver Operating Characteristic Curve in Risk Prediction," Circulation 2007, 115: 928-935. Finally, hazard ratios and absolute and relative risk ratios within subject cohorts defined by a test are a further measurement of clinical accuracy and utility. Multiple methods are frequently used to defining abnormal or disease values, including reference limits, discrimination limits, and risk thresholds.

"Analytical accuracy" refers to the reproducibility and predictability of the measurement process itself, and may be summarized in such measurements as coefficients of variation, and tests of concordance and calibration of the same samples or controls with different times, users, equipment and/or reagents. These and other considerations in evaluating new biomarkers are also summarized in Vasan, 2006.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test, and may be measured by appropriate "performance metrics," such as AUC, time to result, shelf life, etc. as relevant.

"Positive predictive value" or "PPV" is calculated by TP/(TP+FP) or the true positive fraction of all positive test results. It is inherently impacted by the prevalence of the disease and pre-test probability of the population intended to be tested.

"Risk" in the context of the present invention, relates to the probability that an event will occur over a specific time period, as in the responsiveness to treatment, cancer recurrence or survival and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula p/(1−p) where p is the probability of event and (1−p) is the probability of no event) to no-conversion.

"Risk evaluation" or "evaluation of risk" in the context of the present invention encompasses making a prediction of the probability, odds, or likelihood that an event or disease state may occur, the rate of occurrence of the event or conversion from one disease state. Risk evaluation can also comprise prediction of future clinical parameters, traditional laboratory risk factor values, or other indices of cancer, either in absolute or relative terms in reference to a previously measured population. The methods of the present invention may be used to make continuous or categorical measurements of the responsiveness to treatment thus diagnosing and defining the risk spectrum of a category of subjects defined as being responders or non-responders. In the categorical scenario, the invention can be used to discriminate between normal and other subject cohorts at higher risk for responding. Such differing use may require different biomarker combinations and individualized panels, mathematical algorithms, and/or cut-off points, but be subject to the same aforementioned measurements of accuracy and performance for the respective intended use.

"Sensitivity" is calculated by TP/(TP+FN) or the true positive fraction of disease subjects.

"Specificity" is calculated by TN/(TN+FP) or the true negative fraction of non-disease or normal subjects.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is considered highly significant at a p-value of 0.05 or less. Preferably, the p-value is 0.04, 0.03, 0.02, 0.01, 0.005, 0.001 or less.

A "subject" in the context of the present invention is preferably a mammal. The mammal can be a human, non-human primate, mouse, rat, dog, cat, horse, or cow, but are not limited to these examples. Mammals other than humans can be advantageously used as subjects that represent animal models of cancer. A subject can be male or female.

"TN" is true negative, which for a disease state test means classifying a non-disease or normal subject correctly.

"TP" is true positive, which for a disease state test means correctly classifying a disease subject.

"Traditional laboratory risk factors" correspond to biomarkers isolated or derived from subject samples and which are currently evaluated in the clinical laboratory and used in traditional global risk assessment algorithms. Traditional laboratory risk factors for tumor recurrence include for example Proliferative index, tumor infiltrating lymphocytes. Other traditional laboratory risk factors for tumor recurrence known to those skilled in the art.

Methods And Uses Of The Invention

The methods disclosed herein are used with subjects undergoing treatment and/or therapies for a breast cancer, subjects who are at risk for developing a recurrence of breast cancer, and subjects who have been diagnosed with breast cancer. The methods of the present invention are to be used to monitor or select a treatment regimen for a subject who has a breast cancer, and to evaluate the predicted survivability and/or survival time of a breast cancer-diagnosed subject. Treatment regimens include for example but not limited to chemotherapy, radiation therapy, immunotherapy, and combinations of thereof.

Responsiveness (e.g., resistance or sensitivity) of a breast cancer to chemotherapy, radiation therapy, immunotherapy, and combinations of there of is determined by measuring the level of expression of a biomarker in a test sample (e.g., a subject derived sample), and comparing the expression levels to reference or index values, often utilizing mathematical algorithms or formula in order to combine information from results of multiple individual biomarkers and from non-analyte clinical parameters/clinical indicators into a single measurement or index. The biomarker is for example, AE1/AE3 (cytokeratin), TAB250 (Her2-ECD), c-erb B2 (Her2) and phosphorylated Her 2 (pHer2). Clinical indicators include for example data indicating tumor size, multifocalilty, margin status, vessel/perineural invasion, necrosis, histologic type, Bloom-Richardson grade, pTNM and associated pathology including intraductal component, fibrocystic change, and micro-calcifications. The sample is for example a formalin fixed, paraffin-embedded tumor tissue sample.

By resistance is meant that the failure of a cell to respond to an agent. For example, resistance to a chemotherapeutic drug, ionizing radiation, immunotherapy means the cell is not damaged or killed by the drug. By sensitivity is meant that the cell responds to an agent. For example, sensitivity to a chemotherapeutic drug, radiation or immunotherapy means the cell is damaged or killed by the drug.

The methods of the present invention are useful to treat, monitor the progression of or predict the response to therapy in a breast cancer diagnosed subject.

Levels of protein expression of AE1/AE3 (cytokeratin), TAB250 (Her2-ECD), c-erb B2 (Her2) and phosphorylated Her 2 (pHer2) allows for determination of whether a subject will derive a benefit from a particular course of treatment. In this method, a biological sample is provided from a subject before undergoing treatment, e.g., chemotherapeutic, radiation or immunotherapy for breast cancer. By "derive a benefit" it is meant that the subject will respond to the course of treatment. By responding is meant that the treatment that there is a decrease in size, prevalence, or metastatic potential of a breast cancer in a subject. When treatment is applied prophylactically, "responding" means that the treatment retards or prevents a breast cancer or a breast cancer recurrence from forming or retards, prevents, or alleviates a symptom of clinical breast cancer. Assessments of breast cancers are made using standard clinical protocols.

If desired, biological samples are obtained from the subject at various time points before, during, or after treatment. Levels of protein expression of AE1/AE3 (cytokeratin), TAB250 (Her2-ECD), c-erb B2 (Her2) and phosphorylated Her 2 (pHer2) is then determined and compared to a reference value are then identified, e.g. a control individual or population whose breast cancer state is known or an index value. The reference sample or index value may be taken or derived from one or more individuals who have been exposed to the treatment. Alternatively, the reference sample or index value may be taken or derived from one or more individuals who have not been exposed to the treatment. For example, samples may be collected from subjects who have received initial treatment for breast cancer disorder and subsequent treatment for breast cancer to monitor the progress of the treatment.

A reference value can be relative to a number or value derived from population studies, including without limitation, such subjects having the same cancer, subject having the same or similar age range, subjects in the same or similar ethnic group, subjects having family histories of cancer, or relative to the starting sample of a subject undergoing treatment for a cancer. Such reference values can be derived from statistical analyses and/or risk prediction data of populations obtained from mathematical algorithms and computed indices of cancer recurrence. Reference indices can also be constructed and used using algorithms and other methods of statistical and structural classification.

In one embodiment of the present invention, the reference value is the amount of protein expression of AE1/AE3 (cytokeratin), TAB250 (Her2-ECD), c-erb B2 (Her2) and phosphorylated Her 2 (pHer2) in a control sample derived from one or more subjects who are responsive to chemotherapy in breast cancer. In another embodiment of the present invention, the reference value is the amount of protein expression of AE1/AE3 (cytokeratin), TAB250 (Her2-ECD), c-erb B2 (Her2) and phosphorylated Her 2 (pHer2) in a control sample derived from one or more subjects who have higher disease free or overall survival rate from breast cancer. In the other embodiment of the present invention, the reference value is the amount of protein expression of AE1/AE3 (cytokeratin), TAB250 (Her2-ECD), c-erb B2 (Her2) and phosphorylated Her 2 (pHer2) in a control sample derived from one or more subjects who are not at risk or at low risk for developing a recurrence of a breast cancer. In a further embodiment, such subjects are monitored and/or periodically retested for a diagnostically relevant period of time ("longitudinal studies") following such test to verify continued absence of a breast cancer (disease free or overall survival). Such period of time may be one year, two years, two to five years, five years, five to ten years, ten years, or ten or more years from the initial testing date for determination of the reference value. Furthermore, retrospective measurement of protein expression of AE1/AE3 (cytokeratin), TAB250 (Her2-ECD), c-erb B2 (Her2) and phosphorylated Her 2 (pHer2) in properly banked historical subject samples may be used in establishing these reference values, thus shortening the study time required.

A reference value can also comprise the amount of protein expression of AE1/AE3 (cytokeratin), TAB250 (Her2-ECD), c-erb B2 (Her2) and phosphorylated Her 2 (pHer2) derived from subjects who show an improvement in risk factors as a result of treatments and/or therapies for the cancer. A reference value can also comprise the amounts of protein expression of AE1/AE3 (cytokeratin), TAB250 (Her2-ECD), c-erb B2 (Her2) and phosphorylated Her 2 (pHer2) derived from subjects who show an improvement in responsiveness to therapy as a result of treatments and/or therapies for the cancer. A reference value can also comprise the amounts of protein expression of AE1/AE3 (cytokeratin), TAB250 (Her2-ECD), c-erb B2 (Her2) and phosphorylated Her 2 (pHer2) derived from subjects who have higher disease free/overall rate, or are at high risk for developing breast cancer, or who have suffered from breast cancer.

In another embodiment, the reference value is an index value or a baseline value. An index value or baseline value is a composite sample level of protein expression of AE1/AE3 (cytokeratin), TAB250 (Her2-ECD), c-erb B2 (Her2) and phosphorylated Her 2 (pHer2) from one or more subjects who do not have a breast cancer or subjects who are asymptomatic a breast cancer. A baseline value can also comprise level of protein expression of AE1/AE3 (cytokeratin), TAB250 (Her2-ECD), c-erb B2 (Her2) and phosphorylated Her 2 (pHer2) in a sample derived from a subject who has shown an improvement in breast cancer responsiveness to therapy or disease free/overall survival rate as a result of cancer treatments or therapies. In this embodiment, to make comparisons to the subject-derived sample, the amounts of AE1/AE3 (cytokeratin), TAB250 (Her2-ECD), c-erb B2 (Her2) and phosphorylated Her 2 (pHer2) are similarly calculated and compared to the index value. Optionally, subjects identified as having breast cancer, or being at increased risk of developing a breast cancer are chosen to receive a therapeutic regimen to slow the progression the cancer, or decrease or prevent the risk of developing a breast cancer.

The progression of a breast cancer, or effectiveness of a cancer treatment regimen can be monitored by detecting the level of protein expression of AE1/AE3 (cytokeratin), TAB250 (Her2-ECD), c-erb B2 (Her2) and phosphorylated Her 2 (pHer2) samples obtained from a subject over time and comparing the amount of AE1/AE3 (cytokeratin), TAB250 (Her2-ECD), c-erb B2 (Her2) and phosphorylated Her 2 (pHer2) detected. For example, a first sample can be obtained prior to the subject receiving treatment and one or more subsequent samples are taken after or during treatment of the subject. The cancer is considered to be progressive (or, alternatively, the treatment does not prevent progression) if the amount of AE1/AE3 (cytokeratin), TAB250 (Her2-ECD), c-erb B2 (Her2) and phosphorylated Her 2 (pHer2) changes over time relative to the reference value, whereas the cancer is not progressive if the amount of AE1/AE3 (cytokeratin), TAB250 (Her2-ECD), c-erb B2 (Her2) and phosphorylated Her 2 (pHer2) remains constant over time (relative to the reference population, or "constant" as used herein). The term "constant" as used in the context of the present invention is construed to include changes over time with respect to the reference value.

Also provided by the present invention is a method for evaluating changes in the responsiveness to therapy or the rate of disease free/overall survival in a subject diagnosed with cancer, by detecting the level of protein expression of AE1/AE3 (cytokeratin), TAB250 (Her2-ECD), c-erb B2 (Her2) and phosphorylated Her 2 (pHer2) in a first sample from the subject at a first period of time, detecting the level of protein expression of AE1/AE3 (cytokeratin), TAB250 (Her2-ECD), c-erb B2 (Her2) and phosphorylated Her 2 (pHer2) in a second sample from the subject at a second period of time, and comparing the amounts of AE1/AE3 (cytokeratin), TAB250 (Her2-ECD), c-erb B2 (Her2) and phosphorylated Her 2 (pHer2) detected at the first and second periods of time.

Diagnostic, Predictive, and Prognostic Indications of the Invention

The amount of AE1/AE3 (cytokeratin), TAB250 (Her2-ECD), c-erb B2 (Her2) and phosphorylated Her 2 (pHer2) protein can be measured in a test sample and compared to the "normal control level," utilizing techniques such as reference limits, discrimination limits, or risk defining thresholds to define cutoff points and abnormal values. Alternatively, the normal control level can be a database of AE1/AE3 (cytokeratin), TAB250 (Her2-ECD), c-erb B2 (Her2) and phosphorylated Her 2 (pHer2) patterns from previously tested subjects who responded to chemotherapy, radiation therapy or immunotherapy over a clinically relevant time horizon.

The present invention may be used to make continuous or categorical measurements of the response to chemotherapy or cancer survival, thus diagnosing and defining the risk spectrum of a category of subjects defined as at risk for not responding to chemotherapy. In the categorical scenario, the methods of the present invention can be used to discriminate between treatment responsive and treatment non-responsive subject cohorts. In other embodiments, the present invention may be used so as to discriminate those who have an improved survival potential.

Identifying the subject who will be responsive to therapy enables the selection and initiation of various therapeutic interventions or treatment regimens in order increase the individual's survival potential. In this method, a biological sample can be provided from a subject undergoing treatment regimens, e.g., drug treatments for cancer. If desired, biological samples are obtained from the subject at various time points before, during, or after treatment. For example, the invention provides methods of identifying patients who should receive lapatninib (Tykerb). Lapatninib is a small molecule dual kinase inhibitor that seems to work well in these resistant tumors which have high pHer2.

In certain embodiments, the methods of the invention are capable of predicting survivability and/or survival time of a breast cancer diagnosed subject, wherein the subject is predicted to live 3 months, 6 months, 12 months, 1 year, 2, years, 3 years, 4 years, 5 years, 6 years, 7 years, 8 years, 9 years, 10 years, 15 years, 20 years, 30 years, 40 years, or 50 years from the date of diagnosis or date or initiating a therapeutic regimen for the treatment of breast cancer In present invention can also be used to determine the amount of p95HER2 in a formalin fixed, paraffin-embedded tumor tissue sample from the subject For example by the level of protein expression of TAB250 (Her2-ECD), c-erb B2 (Her2) and phosphorylated Her 2 (pHer2) is detected in the sample and the expression levels of Her2 and pHer2 are combined to produce a combined value. The expression level of TAB250 is subtracted from the combined value. By determining the amount of pHER2 in the sample, herceptin sensitivity or resistance can be determined allowing for the appropriate therapy to be selected.

The present invention can also be used to screen patient or subject populations in any number of settings. For example, a health maintenance organization, public health entity or school health program can screen a group of subjects to identify those requiring interventions, as described above, or for the collection of epidemiological data. Insurance companies (e.g., health, life or disability) may screen applicants in the process of determining coverage or pricing, or existing clients for possible intervention. Data collected in such population screens, particularly when tied to any clinical progression to conditions like cancer or cancer progression, will be of value in the operations of, for example, health maintenance organizations, public health programs and insurance companies. Such data arrays or collections can be stored in machine-readable media and used in any number of health-related data management systems to provide improved healthcare services, cost effective healthcare, improved insurance operation, etc. See, for example, U.S. Patent Application No. 2002/0038227; U.S. Patent Application No. US 2004/0122296; U.S. Patent Application No. US 2004/0122297; and U.S. Pat. No. 5,018,067. Such systems can access the data directly from internal data storage or remotely from one or more data storage sites as further detailed herein.

Each program can be implemented in a high level procedural or object oriented programming language to communicate with a computer system. However, the programs can be implemented in assembly or machine language, if desired. The language can be a compiled or interpreted language. Each such computer program can be stored on a storage media or device (e.g., ROM or magnetic diskette or others as defined elsewhere in this disclosure) readable by a general or special purpose programmable computer, for configuring and operating the computer when the storage media or device is read by the computer to perform the procedures described herein. The health-related data management system of the invention may also be considered to be implemented as a computer-readable storage medium, configured with a computer program, where the storage medium so configured causes a computer to operate in a specific and predefined manner to perform various functions described herein.

Performance and Accuracy Measures of the Invention

The performance and thus absolute and relative clinical usefulness of the invention may be assessed in multiple ways as noted above. Amongst the various assessments of performance, the invention is intended to provide accuracy in clinical diagnosis and prognosis. The accuracy of a diagnostic, predictive, or prognostic test, assay, or method concerns the ability of the test, assay, or method to distinguish between subjects responsive to chemotherapeutic treatment and those that are not, is based on whether the subjects have an "effective amount" or a "significant alteration" in the protein expression levels of AE1/AE3 (cytokeratin), TAB250 (Her2-ECD), c-erb B2 (Her2) and phosphorylated Her 2 (pHer2). By "effective amount" or "significant alteration," it is meant that the measurement of an AE1/AE3 (cytokeratin), TAB250 (Her2-ECD), c-erb B2 (Her2) and phosphorylated Her 2 (pHer2) is different than the predetermined cut-off point (or threshold value) and therefore indicates that the subject responsiveness to therapy or disease free/overall survival. The difference in the level of AE1/AE3 (cytokeratin), TAB250 (Her2-ECD), c-erb B2 (Her2) and phosphorylated Her 2 (pHer2) between normal and abnormal is preferably statistically significant.

In the categorical diagnosis of a disease state, changing the cut point or threshold value of a test (or assay) usually changes the sensitivity and specificity, but in a qualitatively inverse relationship. Therefore, in assessing the accuracy and usefulness of a proposed medical test, assay, or method for assessing a subject's condition, one should always take both sensitivity and specificity into account and be mindful of what the cut point is at which the sensitivity and specificity are being reported because sensitivity and specificity may vary significantly over the range of cut points. Use of statistics such as AUC, encompassing all potential cut point values, is preferred for most categorical risk measures using the invention, while for continuous risk measures, statistics of goodness-of-fit and calibration to observed results or other gold standards, are preferred.

Using such statistics, an "acceptable degree of diagnostic accuracy", is herein defined as a test or assay (such as the test of the invention for determining the clinically significant presence of AE1/AE3 (cytokeratin), TAB250 (Her2-ECD), c-erb B2 (Her2) and phosphorylated Her 2 (pHer2) in which the AUC (area under the ROC curve for the test or assay) is at least 0.60, desirably at least 0.65, more desirably at least 0.70, preferably at least 0.75, more preferably at least 0.80, and most preferably at least 0.85.

By a "very high degree of diagnostic accuracy", it is meant a test or assay in which the AUC (area under the ROC curve for the test or assay) is at least 0.80, desirably at least 0.85, more desirably at least 0.875, preferably at least 0.90, more preferably at least 0.925, and most preferably at least 0.95.

The predictive value of any test depends on the sensitivity and specificity of the test, and on the prevalence of the condition in the population being tested. This notion, based on Bayes' theorem, provides that the greater the likelihood that the condition being screened for is present in an individual or in the population (pre-test probability), the greater the validity of a positive test and the greater the likelihood that the result is a true positive. Thus, the problem with using a test in any population where there is a low likelihood of the condition being present is that a positive result has limited value (i.e., more likely to be a false positive). Similarly, in populations at very high risk, a negative test result is more likely to be a false negative.

As a result, ROC and AUC can be misleading as to the clinical utility of a test in low disease prevalence tested populations (defined as those with less than 1% rate of occurrences (incidence) per annum, or less than 10% cumulative prevalence over a specified time horizon). Alternatively, absolute risk and relative risk ratios as defined elsewhere in this disclosure can be employed to determine the degree of clinical utility. Populations of subjects to be tested can also be categorized into quartiles by the test's measurement values, where the top quartile (25% of the population) comprises the group of subjects with the highest relative risk for therapeutic unresponsiveness, and the bottom quartile comprising the group of subjects having the lowest relative risk for therapeutic unresponsiveness Generally, values derived from tests or assays having over 2.5 times the relative risk from top to bottom quartile in a low prevalence population are considered to have a "high degree of diagnostic accuracy," and those with five to seven times the relative risk for each quartile are considered to have a "very high degree of diagnostic accuracy." Nonetheless, values derived from tests or assays having only 1.2 to 2.5 times the relative risk for each quartile remain clinically useful are widely used as risk factors for a disease; such is the case with total cholesterol and for many inflammatory biomarkers with respect to their prediction of future events. Often such lower diagnostic accuracy tests must be combined with additional parameters in order to derive meaningful clinical thresholds for therapeutic intervention, as is done with the aforementioned global risk assessment indices.

A health economic utility function is an yet another means of measuring the performance and clinical value of a given test, consisting of weighting the potential categorical test outcomes based on actual measures of clinical and economic value for each. Health economic performance is closely related to accuracy, as a health economic utility function specifically assigns an economic value for the benefits of correct classification and the costs of misclassification of tested subjects. As a performance measure, it is not unusual to require a test to achieve a level of performance which results in an increase in health economic value per test (prior to testing costs) in excess of the target price of the test.

In general, alternative methods of determining diagnostic accuracy are commonly used for continuous measures, when a disease category or risk category has not yet been clearly defined by the relevant medical societies and practice of medicine, where thresholds for therapeutic use are not yet established, or where there is no existing gold standard for diagnosis of the pre-disease. For continuous measures of risk, measures of diagnostic accuracy for a calculated index are typically based on curve fit and calibration between the predicted continuous value and the actual observed values (or a historical index calculated value) and utilize measures such as R squared, Hosmer-Lemeshow P-value statistics and confidence intervals. It is not unusual for predicted values using such algorithms to be reported including a confidence interval (usually 90% or 95% CI) based on a historical observed cohort's predictions, as in the test for risk of future breast cancer recurrence commercialized by Genomic Health, Inc. (Redwood City, Calif.).

Construction of Clinical Algorithms

Any formula may be used to combine results into indices useful in the practice of the invention. As indicated above, and without limitation, such indices may indicate, among the various other indications, the probability, likelihood, absolute or relative chance of responding to chemotherapy or chemoradiotherapy. This may be for a specific time period or horizon, or for remaining lifetime risk, or simply be provided as an index relative to another reference subject population.

Although various preferred formula are described here, several other model and formula types beyond those mentioned herein and in the definitions above are well known to one skilled in the art. The actual model type or formula used may itself be selected from the field of potential models based on the performance and diagnostic accuracy characteristics of its results in a training population. The specifics of the formula itself may commonly be derived from results in the relevant training population. Amongst other uses, such formula may be intended to map the feature space derived from one or more inputs to a set of subject classes (e.g. useful in predicting class membership of subjects as normal, responders and non-responders), to derive an estimation of a probability function of risk using a Bayesian approach (e.g. the risk of cancer or a metastatic event), or to estimate the class-conditional probabilities, then use Bayes' rule to produce the class probability function as in the previous case.

Preferred formulas include the broad class of statistical classification algorithms, and in particular the use of discriminant analysis. The goal of discriminant analysis is to predict class membership from a previously identified set of features. In the case of linear discriminant analysis (LDA), the linear combination of features is identified that maximizes the separation among groups by some criteria. Features can be identified for LDA using an eigengene based approach with different thresholds (ELDA) or a stepping algorithm based on a multivariate analysis of variance (MANOVA). Forward, backward, and stepwise algorithms can be performed that minimize the probability of no separation based on the Hotelling-Lawley statistic.

Eigengene-based Linear Discriminant Analysis (ELDA) is a feature selection technique developed by Shen et al. (2006). The formula selects features (e.g. biomarkers) in a multivariate framework using a modified eigen analysis to identify features associated with the most important eigenvectors. "Important" is defined as those eigenvectors that explain the most variance in the differences among samples that are trying to be classified relative to some threshold.

A support vector machine (SVM) is a classification formula that attempts to find a hyperplane that separates two classes. This hyperplane contains support vectors, data points that are exactly the margin distance away from the hyperplane. In the likely event that no separating hyperplane exists in the current dimensions of the data, the dimensionality is expanded greatly by projecting the data into larger dimensions by taking non-linear functions of the original variables (Venables and Ripley, 2002). Although not required, filtering of features for SVM often improves prediction. Features (e.g., biomarkers) can be identified for a support vector machine using a non-parametric Kruskal-Wallis (KW) test to select the best univariate features. A random forest (RF, Breiman, 2001) or recursive partitioning (RPART, Breiman et al., 1984) can also be used separately or in combination to identify biomarker combinations that are most important. Both KW and RF require that a number of features be selected from the total. RPART creates a single classification tree using a subset of available biomarkers.

Other formula may be used in order to pre-process the results of individual measurement into more valuable forms of information, prior to their presentation to the predictive formula. Most notably, normalization of biomarker results, using either common mathematical transformations such as logarithmic or logistic functions, as normal or other distribution positions, in reference to a population's mean values, etc. are all well known to those skilled in the art. Of particular interest are a set of normalizations based on Clinical Parameters such as age, gender, race, or sex, where specific formula are used solely on subjects within a class or continuously combining a Clinical Parameter as an input. In other cases, analyte-based biomarkers can be combined into calculated variables which are subsequently presented to a formula.

In addition to the individual parameter values of one subject potentially being normalized, an overall predictive formula for all subjects, or any known class of subjects, may itself be recalibrated or otherwise adjusted based on adjustment for a population's expected prevalence and mean biomarker parameter values, according to the technique outlined in D'Agostino et al, (2001) JAMA 286:180-187, or other similar normalization and recalibration techniques. Such epidemiological adjustment statistics may be captured, confirmed, improved and updated continuously through a registry of past data presented to the model, which may be machine readable or otherwise, or occasionally through the retrospective query of stored samples or reference to historical studies of such parameters and statistics. Additional examples that may be the subject of formula recalibration or other adjustments include statistics used in studies by Pepe, M. S. et al, 2004 on the limitations of odds ratios; Cook, N. R., 2007 relating to ROC curves. Finally, the numeric result of a classifier formula itself may be transformed post-processing by its reference to an actual clinical population and study results and observed endpoints, in order to calibrate to absolute risk and provide confidence intervals for varying numeric results of the classifier or risk formula. An example of this is the presentation of absolute risk, and confidence intervals for that risk, derived using an actual clinical study, chosen with reference to the output of the recurrence score formula in the Oncotype Dx product of Genomic Health, Inc. (Redwood City, Calif.). A further modification is to adjust for smaller sub-populations of the study based on the output of the classifier or risk formula and defined and selected by their Clinical Parameters, such as age or sex.

Combination with Clinical Parameters, Clinical Indicators, Molecular and Morphometric Features Any of the aforementioned Clinical Parameters may be used in the practice of the invention as input to a formula or as a pre-selection criteria defining a relevant population to be measured using a particular biomarker panel and formula. As noted above, Clinical Parameters may also be useful in the biomarker normalization and pre-processing, panel construction, formula type selection and derivation, and formula result post-processing. A similar approach can be taken with the Clinical Indicators, as either an input to a formula or as a pre-selection criterion. In the context of breast cancer, the clinical indicators may include data indicating tumor size, multifocalilty, margin status, vessel/perineural invasion, necrosis, histologic type, Bloom-Richardson grade, pTNM and associated pathology including intraductal component, fibrocystic change, and micro-calcifications.

Embodiments of this invention relate to methods and systems that use computer-generated morphometric information alone or in combination with clinical information and/or molecular information in a predictive model for predicting the occurrence of a medical condition. For example, in one embodiment of the present invention, clinical, molecular and computer-generated morphometric information is used to predict the agressivness of breast cancer and or response to a particular treatment protocol. These predictions may be used by physicians or other individuals to, for example, select an appropriate course of treatment for a patient and/or to diagnose a medical condition in the patient.

In an aspect of the present invention, an analytical tool including a support vector machine (SVM) and/or a neural network may be provided that determines correlations between clinical, molecular, and computer-generated morphometric features and a medical condition. The correlated features may form a model that can be used to predict the occurrence or recurrence of the condition. For example, an analytical tool may be used to generate a predictive model based on data for a cohort of patients whose outcomes with respect to a medical condition (e.g., time to recurrence of cancer, aggressiveness of the cancer, response to therapy) are at least partially known. The model may then be used to evaluate data for a new patient in order to predict the occurrence of the medical condition for the new patient. In some embodiments, only a subset of the three data types (e.g., clinical and morphometric data only) may be used by the analytical tool to generate the predictive model. The clinical, molecular, and/or morphometric data used by embodiments of the present invention may include any clinical, molecular, and/or morphometric data that is relevant to the diagnosis, treatment and/or prediction of a medical condition.

The morphometric data may include computer-generated data indicating various structural and/or spectral properties of, for example, tissue specimens. In one embodiment, the morphometric data may include data for morphometric features of stroma, cytoplasm, epithelial nuclei, stroma nuclei, lumen, red blood cells, tissue artifacts, tissue background, or a combination thereof. In an aspect of the present invention, a tissue image analysis system is provided for obtaining measurements of the morphometric features from a tissue image. Such a system may be the MAGIC™ system which uses the Definiens Cellenger software. Such a system may receive an H&E stained image as input, and may output various measurements of morphometric features for pathological objects in the image. Clinical features may include or be based on data for one or more patients such as age, race, weight, height, medical history, genotype and disease state, where disease state refers to clinical and pathologic staging characteristics and any other clinical features gathered specifically for the disease process at hand. Generally, clinical data is gathered by a physician during the course of examining a patient and/or the tissue or cells of the patient. The clinical data may also include clinical data that may be more specific to a particular medical context. For example, in the context of breat cancer, the clinical data may include data indicatin tumor size, multifocalilty, surgical margin involvement, vessel/perineural invasion, necrosis, histological type, Bloom-Richardson grade, lymph node status, intraductal status, fibrocystics status, micro-calcifications, and/or other clinical data that may be more specific to breast cancer.

The molecular features may include or be based on data indicating the presence, absence, relative increase or decrease or relative location of biological molecules including nucleic acids, polypeptides, saccharides, steroids and other small molecules or combinations of the above, for example, glycoroteins and protein-RNA complexes. For example the expression levels of c-erb B2 (HER2), phosphorylated Her 2 (pHer2), TAB250 (Her2-ECD), AE1/AE3 (cytokeratin) and p95HER are determined. The locations at which these molecules are measured may include glands, tumors, stroma, and/or other locations, and may depend on the particular medical context. Generally, molecular data is gathered using common molecular biological and biochemical techniques including Southern, Western, and Northern blots, polymerase chain reaction (PCR), immunohistochemistry, and immunofluorescence. Further, in situ hybridization may be used to show both the relative abundance and location of molecular biological features. Illustrative methods and systems for in situ hybridization of tissue are described in above-incorporated U.S. patent application Ser. No. 10/624,233, filed Jul. 21, 2003 (now U.S. Pat. No. 6,995,020), and entitled "Methods and compositions for the preparation and use of fixed-treated cell-lines and tissue in fluorescence in situ hybridization."

Measurement Protein Biomarkers

The AE1/AE3 (cytokeratin), TAB250 (Her2-ECD), c-erb B2 (Her2) and phosphorylated Her 2 (pHer2) proteins can be detected in any suitable manner, but is typically detected by contacting a sample from the subject with an antibody which binds the protein, and then detecting the presence or absence of a reaction product.

The antibody may be monoclonal, polyclonal, chimeric, or a fragment of the foregoing, as discussed in detail above, and the step of detecting the reaction product may be carried out with any suitable immunoassay. The sample from the subject is typically a biological fluid as described above, and may be the same sample of biological fluid used to conduct the method described above.

Immunoassays carried out in accordance with the present invention may be homogeneous assays or heterogeneous assays. In a homogeneous assay the immunological reaction usually involves the specific antibody, a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are oligonucleotides, immunoblotting, immunofluorescence methods, immunoprecipitation, quantum dots, multiplex fluorochromes, chemiluminescence methods, electrochemiluminescence (ECL) or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label."

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., 35S, 125I, 131I), enzyme labels (e.g., horseradish peroxidase, alkaline phosphatase), and fluorescent labels (e.g., fluorescein, Alexa, green fluorescent protein, rhodamine) in accordance with known techniques. Highly sensitivity antibody detection strategies may be used that allow for evaluation of the antigen-antibody binding in a non-amplified configuration.

Antibodies can also be useful for detecting post-translational modifications of proteins. Such antibodies specifically detect the phosphorylated amino acids in a protein or proteins of interest, and can be used in immunoblotting, immunofluorescence, and ELISA assays described herein. These antibodies are well-known to those skilled in the art, and commercially available.

The invention also provides for the detection of multiple targets in a sample. Multiple targets include the discrete epitope that the target-binding antibody has affinity for as well as molecules or structures that the epitope is bound to. Thus, multiple target identification includes phenotyping of cells based on the concentration of the same cell surface marker on different cells. In this way multiple target identification is not limited to the discrete epitope that the target binding antibody binds, although this is clearly a way that multiple targets can be identified, i.e. based on the affinity of the target-binding antibody.

Multiple targets are identified by contacting the biological sample with additional antibodies followed by additional labeling reagent specific for the additional antibodies using the method described above. For example, subsets of labeling reagent are prepared with distinct labels, e.g., fluorophores that are distinguished by their emission spectra, e.g., one that emits in the green spectra and one that emits in the red spectra. The labeling reagent subsets are then added to the biological sample containing detection reagent-target complexes in a controlled ratio, e.g., two parts one labeling reagent (e.g., green emission) and one part the other labeling reagent (e.g., red emission) per target binding antibody. In this way the immuno-labeled complexes can be used to detect a target. If another immuno-labeled complex were added to the sample the original target could be distinguished from the subsequently detected target.

The sample is defined to include any material that may contain a target to which an antibody has affinity. Typically the sample is biological in origin and comprises tissue, cell or a population of cells, cell extracts, cell homogenates, purified or reconstituted proteins, recombinant proteins, bodily and other biological fluids, viruses or viral particles, prions, subcellular components, or synthesized proteins. The sample is a biological fluid such as whole blood, plasma, serum, nasal secretions, sputum, saliva, urine, sweat, transdermal exudates, or cerebrospinal fluid. Alternatively, the sample may be whole organs, tissue or cells from an animal. Examples of sources of such samples include muscle, eye, skin, gonads, lymph nodes, heart, brain, lung, liver, kidney, spleen, solid tumors, macrophages, or mesothelium. The sample is prepared in a way that makes the target, which is determined by the end user, in the sample accessible to the immuno-labeled complexes. Typically, the samples used in the invention are comprised of tissue or cells. Preferably, the tissue or cells to be assayed will be obtained by surgical procedures, e.g., biopsy. The tissue or cells are fixed, or frozen to permit histological sectioning. In situ detection is used to determine the presence of a particular target and to determine the distribution of the target in the examined tissue. General techniques of in situ detection are well known to those of ordinary skill. See, for example, Ponder, "Cell Marking Techniques and Their Application," in Mammalian Development: A Practical Approach, Monk (ed.), 115 (1987). Treatments that permeabilize the plasma membrane, such as electroporation, shock treatments, or high extracellular ATP, can be used to introduce reagents into cells.

The methods of the invention provide significant advantages over existing technology in that they do not rely on nucleic acid hybridizations. Therefore, the methods of the invention can be performed in the presence of nucleases e.g., non-specific nucleases, DNase and RNase.

Suitable sources for antibodies for the detection of AE1/AE3 (cytokeratin), TAB250 (Her2-ECD), c-erb B2 (Her2)

and phosphorylated Her 2 (pHer2) include commercially available sources such as, for example, Abazyme, Abnova, Affinity Biologicals, AntibodyShop, Biogenesis, Biosense Laboratories, Calbiochem, Cell Sciences, Chemicon International, Chemokine, Clontech, Cytolab, DAKO, Diagnostic BioSystems, eBioscience, Endocrine Technologies, Enzo Biochem, Eurogentec, Fusion Antibodies, Genesis Biotech, GloboZymes, Haematologic Technologies, Immunodetect, Immunodiagnostik, Immunometrics, Immunostar, Immunovision, Biogenex, Invitrogen, Jackson ImmunoResearch Laboratory, KMI Diagnostics, Koma Biotech, LabFrontier Life Science Institute, Lee Laboratories, Lifescreen, Maine Biotechnology Services, Mediclone, MicroPharm Ltd., ModiQuest, Molecular Innovations, Molecular Probes, Neoclone, Neuromics, New England Biolabs, Novocastra, Novus Biologicals, Oncogene Research Products, Orbigen, Oxford Biotechnology, Panvera, PerkinElmer Life Sciences, Pharmingen, Phoenix Pharmaceuticals, Pierce Chemical Company, Polymun Scientific, Polysiences, Inc., Promega Corporation, Proteogenix, Protos Immunoresearch, QED Biosciences, Inc., R&D Systems, Repligen, Research Diagnostics, Roboscreen, Santa Cruz Biotechnology, Seikagaku America, Serological Corporation, Ab Serotec, SigmaAldrich, StemCell Technologies, Synaptic Systems GmbH, Technopharm, Terra Nova Biotechnology, TiterMax, Trillium Diagnostics, Upstate Biotechnology, US Biological, Vector Laboratories, Wako Pure Chemical Industries, and Zeptometrix.

EXAMPLES

Example 1: General Sample Preparation Methods

The following methods are generally used to during the Multiplex detection methods according to the invention
Antigen Retrieval:
1. De-paraffinize and re-hydrate the tissue samples as per the standard Leica 5020 SOP.
2. Pre-heat 250 ml of 1× Reveal antigen retrieval solution to boiling in water bath in microwave (heat solution for seven (7) minutes at power level seven (7)).
3. Place slides in container of boiling 1× Reveal solution. Allow to boil for 8.0 minutes as described above.
4. When completed, remove container from microwave water bath and allow to cool for 20 minutes.
5. Rinse slides in PBS briefly followed by 1×5 minutes at room temperature.
6. Place slides on Nemesis 7200 and begin auto-staining program.
Tissue Permeabilization:
Incubate slides in PBT (PBS with 0.2% Triton-X) for 30 minutes. PBT is made as follows:

| Reagent | Vendor | Catalog # | Dilution/[Conc.] | Amount | Final Volume |
|---|---|---|---|---|---|
| Difco FA Buffer | Fisher | 223142 | 1X | 1.0 g | |
| Triton-X 100 | Fisher | BP151-500 | 0.2% | 2.0 ml | |
| 20% Tween 20 | BioCare | TWN20H | 1.0% | 50.0 ml | |
| ddH2O | — | — | — | 948.0 ml | 1000 ml |

Autofluorescence Removal:
Incubate slides in acid alcohol (1% HCL in 70% EtOH) for 20 minutes. Acid alcohol is made as follows:

| Reagent | Vendor | Catalog # | Dilution/[Conc.] | Amount | Final Volume |
|---|---|---|---|---|---|
| 200 proof EtOH | Sigma | E7023-4L | 140 proof | 7.28 ml | |
| HCl | Fisher | A144S-500 | 1.0% | 0.1 ml | |
| 20% Tween 20 | BioCare | TWN20H | 1.0% | 0.52 ml | |
| ddH2O | — | — | — | 2.5 ml | 10.4 ml |

Pre-Antibody Treatment Steps

To help permeate the cellular structures of the tissue, the samples are incubated in PBS containing 0.2% Triton-X 100 (PBT) at room temperature for thirty minutes, followed by three rinses of three minutes each in PBS. To help reduce auto-fluorescence in the tissue, the samples are incubated in 1% HCl in 70% ethanol at room temperature for twenty minutes, followed by three rinses of three minutes each in PBS. Blocking of non-specific binding sites is performed by incubating the slides in 1% Blocking Reagent (10.0 mg/ml BSA in PBS) at room temperature for twenty minutes. No washes were performed between the blocking step and the subsequent hybridization step.

Hybridization of Target Specific Antibodies to Biological Samples

Antibodies specific for a target are hybridized for example as follows:

A cocktail of AE1/AE3 (cytokeratin) antibody, TAB250 (Her2-ECD) antibody, c-erb B2 (Her2) antibody and phosphorylated Her 2 antibody is diluted in 1% Blocking Reagent.

| Antibody | Vendor | Catalog # | Dilution | Isotype | Label |
|---|---|---|---|---|---|
| AE1/AE3 | Dako | M3515 | 1:100 | Mouse IgG1 | 488 |
| c-erbB-Intracellular | Dako | A0485 | 1:10 | Rabbit IgG | 594 |
| Her2 TAB250 | Zymed (Invitrogen) | 28-003Z | 1:10 | Mouse IgG1 | 555 |
| Her2-pY-1248 | Dako | M7269 | 1:10 | Mouse IgG1 | 647 |

Approximately 100 µl of this antibody cocktail is applied to the tissue sample, and the antibodies and tissue samples are allowed to hybridize in a humid chamber at room temperature for one hour. Hybridization was followed by two rinses of six minutes each in PBT, one rinse of six minutes in PBS, and one rinse of three minutes in PBS.

Labeling of Hybridized Target Specific Antibodies

Hybridized target specific antibodies are fluorescently labeled for example as follows:

A cocktail of Zenon Alexa Fluor 488 anti-Rabbit IgG Fab fragment and Zenon Alexa Fluor 568 anti-mouse IgG1 Fab fragment (Invitrogen, Carlsbad, Calif.) is made in 1% Blocking Reagent at twice the concentrations recommended by the manufacturer (1:50 dilution for each Fab fragment). Approximately 100 µl of this labeling cocktail is applied to the tissue samples, which are then incubated in a humid chamber at room temperature for 30 minutes. The labeling reaction is followed by two rinses of six minutes each in PBT, one rinse of six minutes in PBS, and one rinse of three minutes in PBS.

Example 2: Multiplex Detection of AE1/AE3 (Cytokeratin), TAB250 (HER2-ECD), C-ERB B2 (HER2) and Phosphorylated HER 2 (PHER2)

AE1/AE3 (cytokeratin), TAB250 (Her2-ECD), c-erb B2 (Her2) and phosphorylated Her 2 (pHer2) have been found to be important biomarkers for the evaluation of breast cancerous tissue. The qualitative and quantitative distribution of these markers in formalin fixed, paraffin embedded tissue sections or Tissue Microarrays were detected as described below. Breast tumor cell lines MCF7, T47D and SBR3 or formalin fixed paraffin embedded (FFPE) tissue samples from patients with known HER2 status were used. Twenty-six patients (52 cores) were used for analysis. c-erbB2 and pHER2 were univariately associated with HercepTest results and both were selected in a model to discriminate Her2 (2+) from Her2 (3+) with an AUC: 0.92, sensitivity 0.90, specificity 0.85

1.) Antigen Retrieval (in Reveal Solution, Citrate Buffer or Proteinase K)

For antigen retrieval, tissue sections or TMAs are heated in 1× Reveal Solution (BioCare Medical) in a decloaking chamber according to standard protocol and then allowed to cool for 15 minutes. Alternative methods of antigen retrieval include: 1) heating tissue sections or TMAs in 10 mM Citrate Buffer, pH6.0, for 15 minutes in a calibrated microwave followed by cooling for 15 minutes or 2) enzymatically digesting tissue sections or TMAs in a Proteinase K solution (commercially available from Fisher as a Ready-to-Use reagent for antigen retrieval for 12-15 minutes. After rinsing in distilled water for 15 minutes (this step is skipped for Proteinase K antigen retrieval), the slides were washed 3×5 minutes in Phosphate Buffered Saline (PBS).

2.) Autofluorescence Removal

Autofluorescence was reduced by incubating the slides in 1% HCl/70% EtOH for 10 minutes at room temperature. Slides were then rinsed 3×5 minutes in PBS.

3.) Tissue Permeabilization

Tissue are subsequently permeabilized in PBS containing 0.2% Triton X (PBT) for 30 minutes at room temperature.

4.) Blocking with Unspecific IgG

Non-specific binding of antibody or Fab fragment was be blocked by incubation with 0.5 μg/ul BSA in PBT for 20 minutes in a humidity chamber. Slides are subsequently rinsed in PBT for 5 minutes.

6.) Incubation of Untreated Primary Antibodies on Tissue

Antibody is incubated on the tissue for 1 hour at room temperature in a humidity chamber.

7.) Removal of Unbound Antibody

Excess antibody is removed by washing the slides 2×10 minutes in PBT followed by 3×5 minutes in PBS.

8.) Incubation with Fluorescently Labeled Fab

Mouse and Rabbit specific Fab fragment labeled with Alexa 555 and Alexa 594 respectively are added to the slide and incubated for 30 minutes at room temperature in a humidity chamber.

9.) Removal of Unbound Fab

Unbound Fab fragment is removed by washing the slides 2×10 minutes in PBT followed by 3×5 minutes in PBS.

10.) Fixation

Tissue are fixed in 10% formalin for 10 minutes. Slides were rinsed 2×5 minutes in PBS.

11.) Mounting

After adding 100 μl AntiFade solution containing nuclear counterstain, slides are coverslipped and prepared for imaging capture.

12.) Image Acquisition

Samples are placed on a 90i automated fluorescent microscope. Regions of interest are identified by moving the y-x axes of the microscope stage. Image exposure time was set to the highest possible brightness level without causing overexposure. Images are acquired with the Nikon 1200DXM CCD camera or comparable system (alternatively a spectral imaging camera might be used for advanced spectral separation of fluorescent dyes). Images are saved in tiff format and subjected to quantitative image analysis.

13.) Results

A. Univariate analyzed each of the predictors for the two endpoints (Her2 2+ vs 3+ and FISH+ vs −)

| endpoint | feature | Wald (chi-sq) | p-value |
|---|---|---|---|
| Her2 | pY Her-2 | 6.977 | 0.0083 |
| Her2 | Her-2 (A0485) | 12.058 | 0.0005 |
| Her2 | TAB250 | 9.915 | 0.0016 |
| Fish | pY Her-2 | 3.948 | 0.0469 |
| Fish | Her-2 (A0485) | 6.619 | 0.0101 |
| Fish | TAB250 | 8.618 | 0.0033 |

Figure 2:
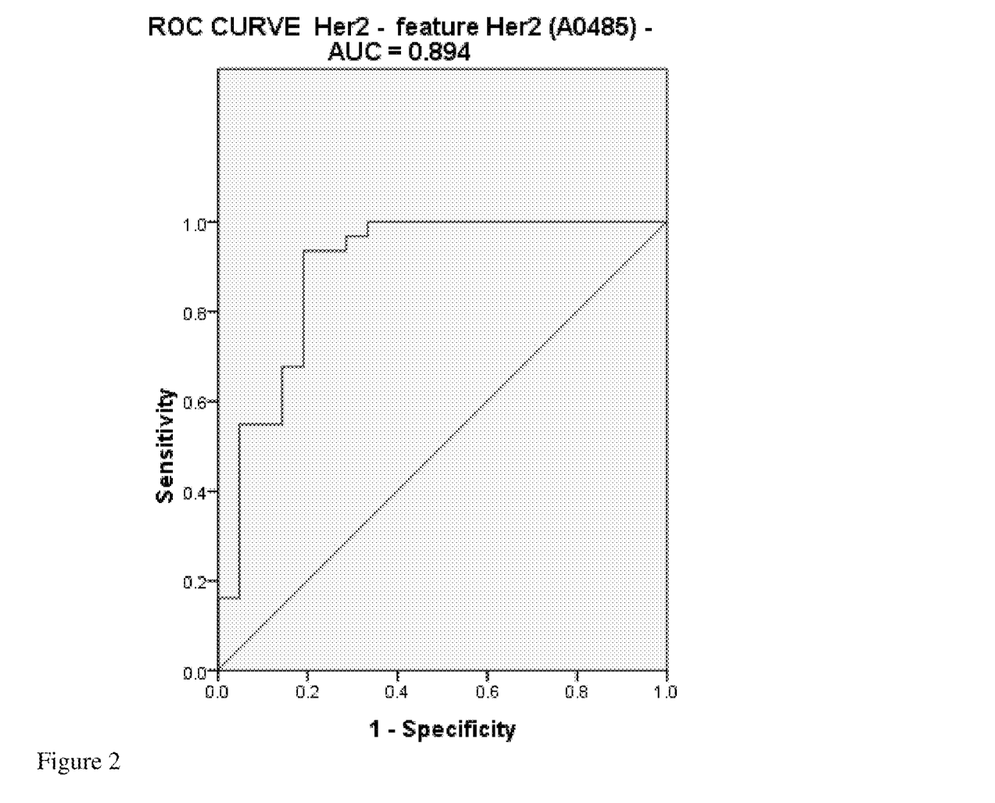
FIG. 2 is an ROC curve showing immunoflourescence (IF) of c-erbB2 HER2 to distinguish between Her2 (+) 2+(HercepTest) from Her2 3+(HercepTest) individuals.

B) Development of a cutpoint for each feature for both endpoints and calculated the accuracy of that the chi-square and associate p-value and the AUC of the classification (FIG. 2)

| endpoint | feature | cutpoint | Wald (chi-sq) | p-value | AUC |
|---|---|---|---|---|---|
| Her2 | pY Her-2 | 408787 | 18.907 | <0.0001 | 0.8402 |
| Her2 | Her-2 (A0485) | 160069 | 20.139 | <0.0001 | 0.8925 |
| Her2 | TAB250 | 1120000 | 20.268 | <0.0001 | 0.8641 |
| Fish | pY Her-2 | 334021 | 16.386 | 0.0001 | 0.8542 |
| Fish | Her-2 (A0485) | 134250 | 20.748 | <0.0001 | 0.9097 |
| Fish | TAB250 | 1320000 | 16.386 | 0.0001 | 0.8542 |

Figure 1:
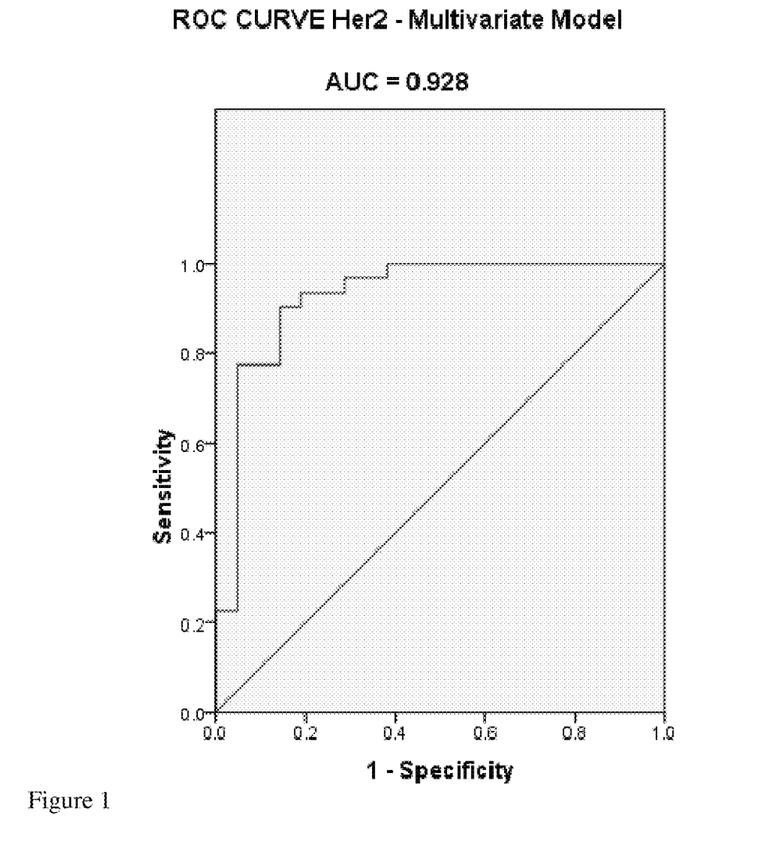
FIG. 1 is an ROC curve showing a multivariate model of IF Her2 and IF pHer2 to distinguish between Her2 2+(HercepTest) from Her2 3+(HercepTest) tumor specimens (individuals).

C) Multivariate models (with feature selection) for each endpoint: Her2 endpoint (FIG. 1)

| AUC | 0.928 |
|---|---|
| Sensitivity | 0.903 |
| Specificity | 0.857 |

| Feature | weight |
|---|---|
| pY Her-2 | 3.0588 |
| Her-2 (A0485) | 5.2093 |

Figure 3:
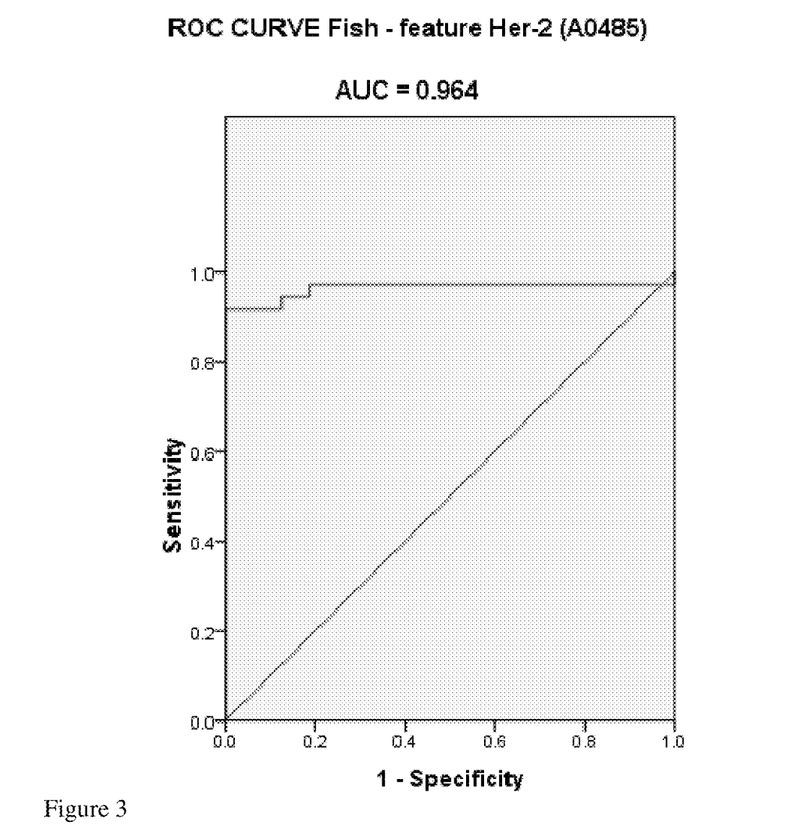
FIG. 3 is an ROC curve showing a multivariate model of IF Her2 (c-erbB2) as the only feature selected to distinguish Her2 FISH+ from Her2 FISH (−) tumor specimens (individuals).

FISH endpoint (FIG. 3)

| AUC | 0.964 |
|---|---|
| Sensitivity | 0.917 |
| Specificity | 1 |

| Feature | weight |
|---|---|
| Her-2 (A0485) | 3.19188 |

Example 3: Extrapolation of P95 Levels

There is no commercially available antibody for the truncated (p95) Her2 receptor which works well in formalin-fixed, paraffin-embedded tissue samples. Given the significance of p95 in Herceptin resistance it was sought to utilize the existing reagents employed in the currently described multiplex of the invention to examine the localization, distribution and level of p95 in breast tumor samples. To identify p95 in breast cancer specimens we combined the intensity values (i.e. fluorescent based pixel determination) of both the full length (i.e. Her2-A0485) and phosphorylated (Her2-pY1248) forms of Her2—which are both cytoplasmic—and then subtracted the measured intensity level of the Her2 antibody which recognizes the extracellular domain (TAB250) of the full length receptor. By performing this calculation we hypothesized that the resulting value would represent the truncated p95 form (+/−phosphorylation). P95 levels have been associated with herceptin resistance and therefore is indicative of a patients response to therapies such as lapatinab.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for administering a course of treatment to a subject with a cancer type comprising the steps of:
   A. measuring, using an immunofluorescence imaging device having a connection to a computing device configured to execute code in a processor, at least a plurality of protein expression levels of the subject by contacting a formalin fixed paraffin-embedded tissue sample of the subject to antibodies of Her2, Her2-ECD, cytokeratin and p95HER2;
   B. capturing an image of the tissue sample with the immunofluorescence imaging device and analyzing the image with an image analysis device to determine plurality of protein expression levels present in the sample;
   C. automatically storing the plurality of protein expression levels measured by the image analysis device in a subject dataset in a memory of the computing device wherein the subject dataset includes clinical and biographic data relating to the subject;
   D. calculating, using the computing device, a protein expression level of p95HER2 for the subject according to a function (1);
      i. where function (1)=p95HER2=(Her2+pHer2)−Her2−ECD;
   E. providing a machine learning application with a population dataset from a data storage device, wherein the machine learning application is configured to generate an effective treatment model using a linear discriminant analysis on the population dataset, wherein the population dataset includes data relating to each member of the population obtained at least two different points in time, wherein each member is diagnosed with the same cancer type and similar clinical features as the subject and the data obtained at the at least two different points in time relating to each member includes:
      i. at least one data value corresponding to treatment resistance status,
      ii. at least one data value corresponding to treatment status;
      iii. at least one data value corresponding to the health outcome,
      iv. and the protein expression levels for each individual as obtained by:
         1. contacting a formalin fixed paraffin-embedded tissue sample of each member of the population with antibodies to Her2, Her2-ECD, cytokeratin, p95HER2 and p95HER2 for each member of the population dataset, and
         2. deriving the protein expression level of p95HER2 of each member of the population dataset according to function (1);
   F. evaluating the subject dataset with the effective treatment model, wherein the evaluation yields a value related to a probability that the subject will have a resistance to at least one treatment for the cancer type;
   G. generating, using a treatment module configured as instructions for the computer, a output data object that includes at least information indicating a course of treatment for the subject that does not include any treatment where the probability that the subject will have resistance is above a given threshold.

2. The computer implemented method of claim 1, wherein the antibodies of step (A) are selected from AE1/AE3 (cytokeratin), TAB250 (Her2-ECD), c-erb B2 (Her2) and an antibody to phosphorylated Her 2 (pHer2).

3. The computer implemented method of claim 1, wherein the discriminant analysis of step (E) is an Eigengene-based Linear Discriminant analysis implemented to determine the relationship between protein expression values found in the population dataset and treatment resistance status.

4. The computer implemented method of claim 1, wherein the subject and population datasets include morphometric measurement data obtained from an image analysis appliance.

5. The method of claim 4, wherein the morphometric measurement data are obtained by the steps of:
   1) accessing with an image access module configured as code executing in a processor, a first set of tissue images associated with the subject of the subject dataset of step (C);
   2) accessing with an image access module configured as code executing in a processor, a second set of tissue images associated with the each member of the population dataset of step (E); and
   3) obtaining morphometric measurements for the first and second sets of tissue images using a morphometric analysis module configured as code executing in the processor.

6. The method of claim 1, wherein the course of treatment of step (G) comprises administering lapatinib.

7. The method of claim 1, wherein the course of treatment of step (G) comprises administering immunotherapy.

8. The method of claim 7, wherein the treatment comprises at least one of trastuzumab and bevacizumab.

9. The method of claim 1, wherein the generating a course of treatment of step (G) further comprises:
   assigning the subject, based on the evaluation of the population dataset, to at least one of a plurality of survivability categories, and assigning the subject, based on the survivability category, to one of a plurality of treatment categories, wherein assigning the subject to at least one of a plurality of treatment categories comprises determining, based on the amount of pHER2 in the tissue sample from the subject, at least one of (a) trastuzumab sensitivity and (b) trastuzumab resistance.

10. The method of claim 1, wherein the course of treatment generated in step (G) is based on the probability of at least one of (a) trastuzumab sensitivity and (b) trastuzumab resistance is above a given threshold value.

11. The method of claim 1, further comprising generating a plurality of treatment options wherein each of the plurality of treatment options correspond to a treatment where the probability that the subject will have resistance to that treatment is below a given threshold.

12. The method of claim 1, wherein the population dataset of step (E) includes data obtained from one or more individuals who have been exposed to the particular course of treatment.

13. The method of claim 1, wherein the population dataset of step (E) includes data obtained from one or more individuals who have not been exposed to the particular course of treatment.

14. The method of claim 1, wherein the population dataset of step (E) comprises at least one of:
 (a) one or more individuals who are responsive to chemotherapy in breast cancer;
 (b) one or more individuals who have a higher disease free survival rate from breast cancer;
 (c) one or more individuals who have a higher overall survival rate from breast cancer;
 (d) one or more subjects who are not at risk for developing a recurrence of breast cancer; and
 (e) one or more subjects who are at a low risk for developing a recurrence of breast cancer.

15. A method for administering a course of treatment to a subject with a cancer type comprising the steps of:
 A. measuring, using an immunoassay, at least a plurality of protein expression levels of the subject by contacting a formalin fixed paraffin-embedded tissue sample of the subject to antibodies of Her2, Her2-ECD, cytokeratin and pHER2;
 B. storing the plurality of protein expression levels as data values in a subject dataset stored in a data storage device;
 C. calculating, using the computer configured to access the subject dataset, a protein expression level of p95Her2 for the subject according to a function (1);
  i. where function (1)=p95Her2=(Her2+pHer2)−Her2−ECD;
 D. providing a machine learning application configured, to generate an effective treatment model using a linear discriminant analysis on a population dataset, wherein the population dataset includes at least data relating to individuals diagnosed with the same cancer type as the subject, at least one treatment resistance status for each individual, and the protein expression levels for each individual as obtained by:
  i. contacting a formalin fixed paraffin-embedded tissue sample of each member of the population dataset with antibodies to Her2, Her2-ECD, cytokeratin, p95Her2 and pHER2, and
  ii. deriving the protein expression level of p95Her2 of each member of the population dataset according to function (1);
 E. evaluating the subject dataset with the effective treatment model, wherein the evaluation yields a value related to a probability that the subject will have a resistance to at least one treatment for the cancer type; wherein the evaluation includes identifying at least one hyperplane that separates at least a first class of disease resistance from at least a second class of disease resistance using the population dataset and locating the subject at a distance from the at least one hyperplane, the probability that the subject will have a resistance to at least one treatment corresponding to the distance of the subject from the at least one hyperplane; and
 F. generating, using a treatment module configured as instructions for the computer, a course of treatment for the subject that does not include any treatment where the probability that the subject will have resistance is above a given threshold.

16. The computer-implemented method of claim 15 further comprising the steps of:
 G. updating the subject dataset of step (B) and the population dataset of step (D) over a plurality of time periods;
 H. generating a revised effective treatment model based on the comparison of the updated subject dataset of step (B) and population dataset of step (D) and
 I. generating a revised course of treatment based on the comparison of the updated first and second datasets.

17. The computer-implemented method of claim 16, wherein the revised treatment effective treatment model comprises generating at least a revised course of treatment regimen for administering to the subject a given amount of a medication for a period of time.

18. The method of claim 16, wherein updating the subject database over time comprises determining, based on one or more changes, that a cancer is progressive, wherein the one or more changes comprise one or more changes in an amount of cytokeratin and Her2 as determined by contacting antibodies to cytokeratin, Her2-ECD, Her2 and phosphorylated Her 2 with a plurality of samples from the subject over time relative to the population dataset of step (D).

* * * * *